US010119952B2

(12) United States Patent
Chen et al.

(10) Patent No.: US 10,119,952 B2
(45) Date of Patent: Nov. 6, 2018

(54) INLINE WATER CONTAMINANT DETECTOR AND FILTER

(71) Applicant: Ecomo Inc., Sunnyvale, CA (US)

(72) Inventors: Gang Chen, Coraopolis, PA (US); Zhiqiang Li, Herndon, VA (US)

(73) Assignee: SHENZHEN YIMU TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/458,189

(22) Filed: Mar. 14, 2017

(65) Prior Publication Data

US 2017/0199169 A1 Jul. 13, 2017

Related U.S. Application Data

(63) Continuation-in-part of application No. 15/174,809, filed on Jun. 6, 2016.

(Continued)

(51) Int. Cl.

| G01N 33/18 | (2006.01) |
|---|---|
| G01N 21/33 | (2006.01) |
| B01D 29/60 | (2006.01) |
| B01D 29/96 | (2006.01) |
| B01D 35/143 | (2006.01) |
| C02F 1/00 | (2006.01) |
| C02F 1/28 | (2006.01) |
| G01N 21/59 | (2006.01) |
| G01N 21/85 | (2006.01) |
| G01N 21/51 | (2006.01) |

(52) U.S. Cl.
CPC .............. *G01N 33/18* (2013.01); *B01D 29/60* (2013.01); *B01D 29/96* (2013.01); *B01D 35/143* (2013.01); *C02F 1/003* (2013.01); *C02F 1/283* (2013.01); *G01N 21/33* (2013.01); *G01N 21/59* (2013.01); *G01N 21/85* (2013.01); *G01N 33/1826* (2013.01); *C02F 2209/06* (2013.01); *C02F 2209/10* (2013.01); *C02F 2209/20* (2013.01); *C02F 2307/06* (2013.01);

(Continued)

(58) Field of Classification Search
CPC ...... B01D 29/60; B01D 29/96; B01D 35/143; C02F 1/003; C02F 1/283; C02F 2209/06; C02F 2209/10; C02F 2209/20; C02F 2307/06; G01N 2021/8571; G01N 21/59; G01N 21/85; G01N 2201/062; G01N 33/18
See application file for complete search history.

(56) References Cited

U.S. PATENT DOCUMENTS 5,527,451 A * 6/1996 Hembree .............. B01D 24/008
   210/100
5,891,329 A * 4/1999 Massholder ............ C02F 1/325
   210/100

(Continued)

*Primary Examiner* — Marcus Taningco
(74) *Attorney, Agent, or Firm* — Chan Hubbard PLLC; Keala Chan

(57) ABSTRACT

An affordable, low-power, low-profile water contamination detection and/or filtration device that can be installed directly onto a home faucet or other water line. The contamination detection part uses photometric and other sensors to collect data pertaining to levels of Total Organic Carbon, Total Dissolved Solids, heavy metals, turbidity, harmful bacteria, and other contaminants. The device uses efficient circuit design so that parts of the sensor, LED, and calculation circuit are only activated when the faucet is turned on and water fills a measurement chamber. The filtration part of the device can be switched on and off using simple twist interface, such that filtered water can flow directly into the contamination detection part for testing.

8 Claims, 10 Drawing Sheets

Related U.S. Application Data

(60) Provisional application No. 62/172,119, filed on Jun. 7, 2015.

(52) U.S. Cl.
CPC ..... *G01N 21/51* (2013.01); *G01N 2021/8571* (2013.01); *G01N 2201/062* (2013.01); *Y02A 20/206* (2018.01)

(56) References Cited

U.S. PATENT DOCUMENTS

| | | | | |
|---|---|---|---|---|
| 5,993,648 A * | 11/1999 | Hunter | ............... | B01D 17/0202 137/801 |
| 6,264,830 B1 * | 7/2001 | Plester | ................... | C02F 9/005 210/103 |
| 6,495,049 B1 * | 12/2002 | Van Esch | ................ | C02F 9/005 210/103 |
| 7,326,334 B2 * | 2/2008 | Boyd | ..................... | B01D 35/04 210/419 |
| 2005/0139552 A1 * | 6/2005 | Forsberg | ................... | E03B 3/28 62/635 |
| 2005/0160620 A1 * | 7/2005 | Morgan | .................. | F26B 9/066 34/469 |
| 2014/0202962 A1 * | 7/2014 | Bilenko | .................. | C02F 1/325 210/748.11 |
| 2016/0052798 A1 * | 2/2016 | Downs | .................... | C02F 1/008 210/742 |

* cited by examiner

INLINE WATER CONTAMINANT DETECTOR AND FILTER

CROSS-REFERENCE TO RELATED APPLICATIONS

This Application is a continuation-in-part of U.S. patent application Ser. No. 15/174,809, filed on Jun. 6, 2016, which claims the benefit of priority to U.S. Patent Appl. No. 62/172,119, filed on Jun. 7, 2015.

FIELD OF THE INVENTION

The invention relates to the field of water contaminant detectors and filters.

BACKGROUND OF THE INVENTION

Water safety and purity is a civic necessity of utmost importance. Human health and safety dictates that drinking and other home use water must meet various health and environmental standards. Contaminated equipment or fluids at various sources in the water supply can affect thousands of homes and lives. Sabotage and attacks on the water supply must not only be prevented, but rapidly detected. Consumers feel increasingly insecure about the water in their home taps. Despite water purification by state and local municipalities, many consumers install filtration systems in order to purify their water.

Public water utilities and state and local agencies typically perform contaminant detection at water treatment centers, public water supplies and wells, and other central locations in the water distribution system by grab sampling, which means that technicians collect field samples or perform measurements in the field. A common analytic technique for measuring water quality is to determine the level of Total Organic Carbon ("TOC") in the water. TOC can come from decaying organic matter or synthetic sources such as industrial chemicals or fertilizers, and as such is an indicator of water quality.

Typical TOC analyzers are large and expensive devices that are best suited for utilization on-site at central locations in the water supply. Some devices burn the sample in a furnace then analyze remaining $CO_2$, which is directly proportional to the amount of carbon in the sample. More recently, UV254 has been used as a TOC substitute, wherein the amount of UV254 absorbed by the water is known to be proportional to the concentration of organic carbon matter in the water. Devices that use UV254 typically use a large light source with large power requirement, for high accuracy measurement. Furthermore, these instruments use a standing sample of water, to further increase their accuracy.

Other water contaminants that consumers seek to detect and filter include heavy metals, Total Dissolved Solids (TDS), turbidity, and other bacteria. Many types of filters are commercially available to trap and remove pollutants such as organic and man-made chemicals, heavy metals, sediments, radioactive isotopes, etc. Such filters come in many forms, including activated carbon, carbon block, reverse osmosis, and ion exchange filters. Typical commercially available consumer filters are contained within water pitchers, installable onto faucets and taps, and some are incorporated into the building's plumbing.

SUMMARY OF THE INVENTION

The invention is the first affordable, low-power, low-profile device that can be installed directly onto a home faucet or other water line, enabling contamination detection in real-time. Instead of relying exclusively on municipal testing for ascertaining water contamination, residents can now test for TOC and other contaminants directly from their own tap. Instead of purchasing water filtration systems and/or bottled water, consumers can now rely upon a device installed on their own tap for integrated detection and filtration. In addition, the device incorporates a replaceable filter that can be switched on and off as needed, so that the user can filter water for drinking or let water flow unfiltered for other uses.

The device comprises a measurement part that identifies contaminants in a flow of water from the tap. Water is diverted from the flow of the tap into a sampling chamber where turbulence is minimized. When the sampling chamber is sufficiently full of water, one or more electronic receivers disposed in or around the sample chamber is automatically activated to collect data regarding the water in the chamber. This data is processed by an efficient integrated circuit and then transmitted for display, either externally on the surface of the device, or wirelessly to a user's mobile device.

Minimal turbulence in the sampling chamber, automatic activation, highly efficient integrated circuit, and optional redundant data collection all contribute to the accuracy of the contaminant calculation, and to the ability to build the device to low power specifications. The result is a small and efficient device that is simple to package, ship, handle, install and use with consumer taps.

An application can be installed to a user's personal mobile device with an application for displaying a variety of contamination information to the user. This information can include, but is not limited to, the level of each type of contaminant detected in the water, comparisons to recommended safety levels, water filter replacement recommendations, and locations of water contamination events as detected by similar devices installed by other consumers. It can also convey information about the device itself, such as the status of the water filter and whether the filter needs to be replaced. The application may send and receive data from a server for storage and retrieval of water contamination data. A central repository of water contamination data from the described devices may help governments and municipalities identify and solve problems in the water supply.

DETAILED DESCRIPTION

Figure 1:
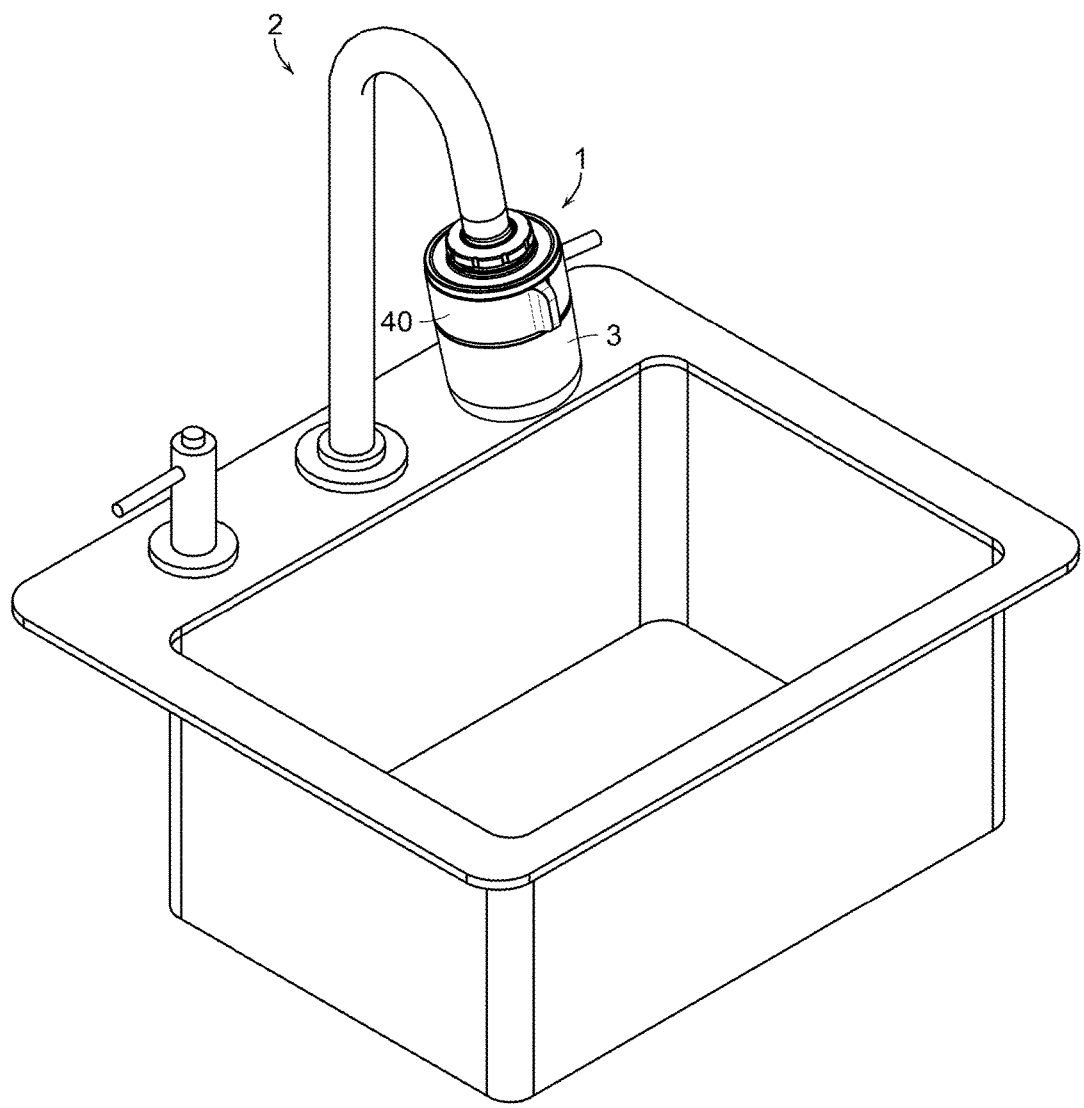
FIG. 1 is a depiction of an embodiment of the device in an environment of use.

As noted in the Background, typical water contaminant detectors are large devices that are applied to standing water. Consumers have no means to monitor contaminants in their own residences or commercial spaces. An installable device 1 is described that can be installed directly onto a tap 2. An example of the device in the consumer tap environment is shown in FIG. 1. The device comprises a measurement unit 3 and can optionally also comprise a filter unit 40. The measurement unit contains functionality to detect and monitor contaminants inside the water, while the filter unit functions to filter contaminants out.

The filter unit comprises a compartment 43 holding replaceable filter 49 that can be utilized when activated by rotating the filter unit using external switch 42. Using the device installed directly onto their tap, the user can filter water, test the filtered water for impurities, and test unfiltered water for impurities, all seamlessly from the tap.

Measurement Unit

Figure 4:
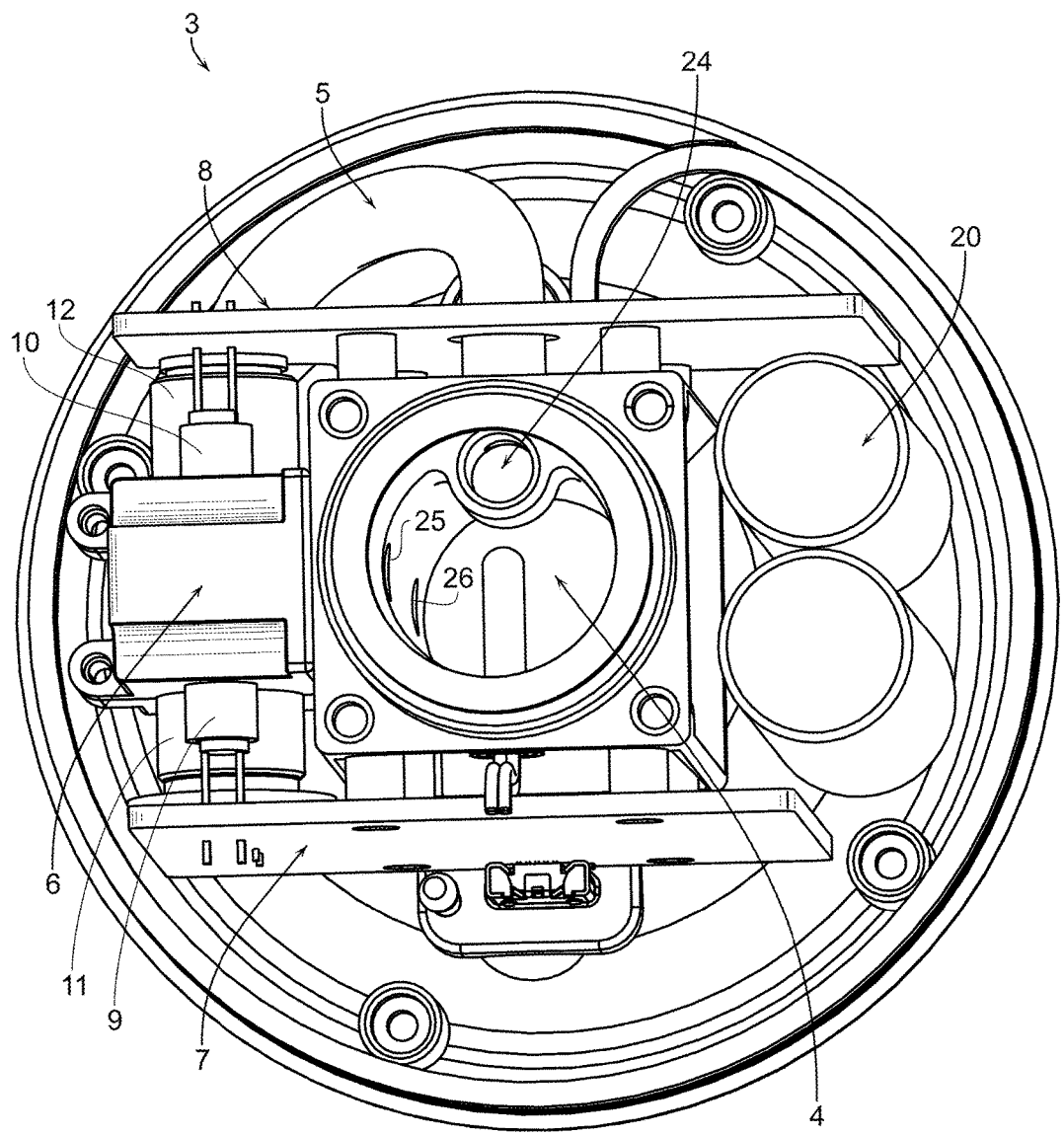
FIG. 4 is a top view, in partial perspective, of the inside of an embodiment of the device.

When the tap 2 is operated, water flows through the device and into entrance 4. As shown in FIG. 4, most of the water will flow through the measurement unit entrance 4, but a portion of the flow will enter diversion opening 24, which diverts water flow through a conduit 5 into a measurement chamber 6. The device comprises one or more electronic receivers, e.g. 11 and 12, for receiving information about the fluid within the chamber 6.

Figure 3:
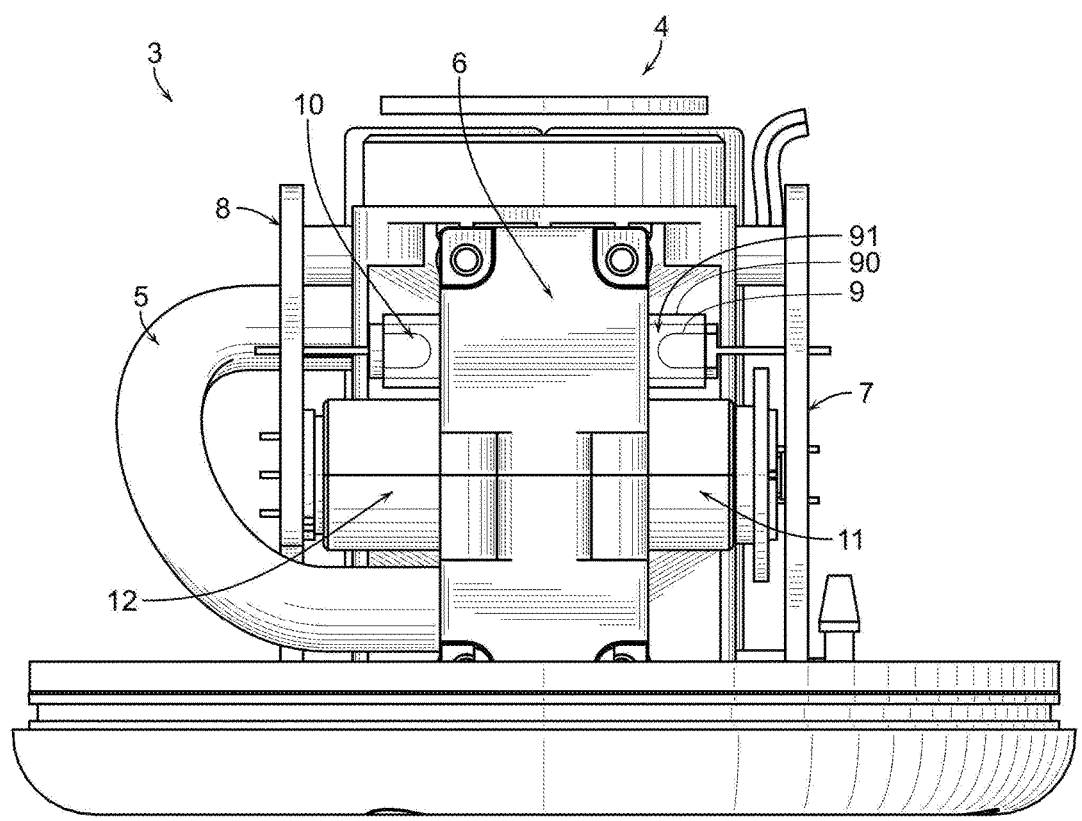
FIG. 3 is a side view of the inside of an embodiment of the device.

Efficiency and accuracy of the one or more electronic receivers is facilitated by reducing the turbulence of fluid within the chamber 6. In the preferred embodiment, as demonstrated in FIG. 4, water flows into chamber 6 from the base of said chamber to fill. Whereas a downward waterfall of fluid would cause air bubbles and turbulence, water flow from the base of the chamber causes air bubbles and turbulence to be minimized. Reduction of turbulence, air and other causes of refraction results in more efficient and accurate measurement of light by photometric sensors. Yet the water need not flow into the base of the chamber to achieve this result. For instance, water flow from the top of the chamber may be slowed by a buffer. As another example, the chamber may be shaped to facilitate the dissipation of air bubbles, such as by having a large horizontal cross-section at the top. And while the device illustrated here is installed into a tap water faucet, it is contemplated that the device could be installed in different parts of the water line wherein it may comprise a different conduit for diversion of water flow. Furthermore, the conduit 5 depicted in FIGS. 3 and 4 is tubular in order to illustrate the diversion of flow more clearly, but may obviously take on any shape or form. Finally, as would obviously be necessary to return water to the flow out of the tap for drinking or use, the chamber can also comprise one or more exits 25 and/or 26.

Figure 2:
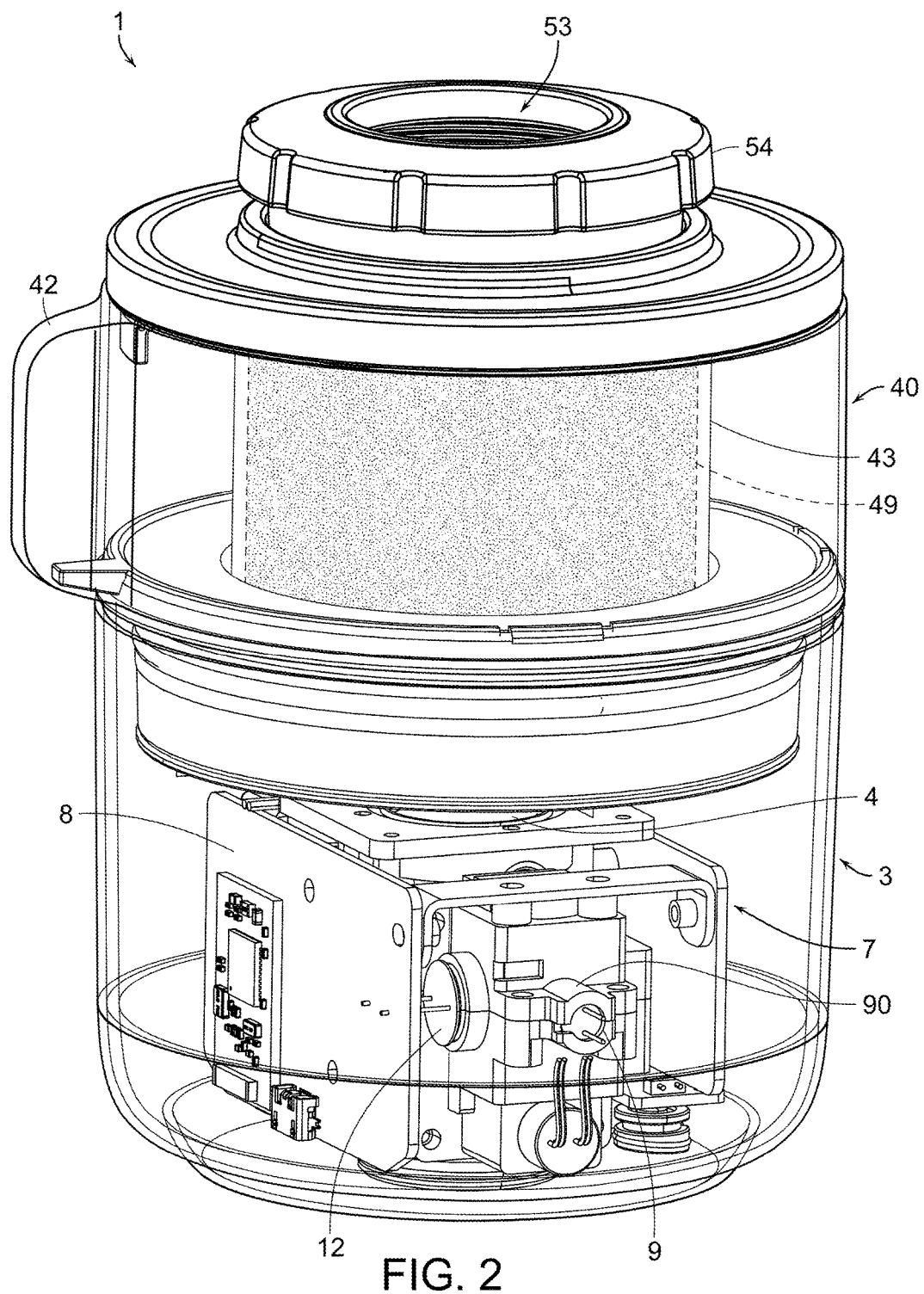
FIG. 2 is a side view, in partial perspective, some parts being depicted with transparency.

The system also comprises one or more LEDs, such as 9 and 10, situated in or near chamber 6 to emit light into the chamber. At least one of the receivers is a photometric sensor that measures light absorption of the fluid when the chamber is substantially full. As noted above, reduction in turbulence and air in the water greatly facilitates the operation of photometric sensors that receive light passing through the water. LEDs are known to have low power requirements, further minimizing the size and energy needed by the device. The sample chamber 6 is preferably a quartz cuvette, or similarly comprised of a material known for high conductivity of UV254, to increase the accuracy of photometric measurements from the chamber. The LEDs and receivers can be located anywhere around chamber 6, not necessarily on opposite sides. For instance, LED 9 is located at a right angle to receiver 12 in the embodiment depicted in FIG. 2. In order to further increase the accuracy of the light absorption measurements of the one or more receivers the LED can be enclosed within a solid casing 90 with small opening 91 near the chamber, so that light is directed through the chamber and prevented from reflection or diffusion by the external surface of the chamber.

The preferred embodiment uses ultraviolet light absorption, preferably at a wavelength of 254 nm (UV254), to correlate with and therefore measure Total Organic Carbon (TOC) contaminants in the water. Ultraviolet wavelengths in the range of 250 to 300 nm are known to be closely correlated to TOC levels, UV254 having a high adjusted coefficient of determination of 0.997.

A photometric sensor can also be used to measure infrared (IR), which is an indicator of turbidity. IR correlates to turbidity, which is a type of contaminant data, but the IR absorption can also be used to refine TOC calculation. Furthermore, a temperature probe situated in or near the cuvette may further refine the calculation to account for changes in light strength due to temperature fluctuations. TOC can be determined according to the following formula:

$$TOC = K_{toc} * K_{D2*} * D2 * \lg(A0*(1-Ka*T)/D1)$$

Where $K_{toc}$ is the TOC coefficient, $K_{D2*}$ is the IR turbidity coefficient, D2 is the turbidity ADC measurement, A0 is UV intensity at 0° C., Ka is the UV/temperature intensity coefficient, T is temperature, and D1 is the UV TOC ADC measurement. The TOC coefficient may be adjusted to account for the ultraviolet wavelength actually used.

Figure 6:
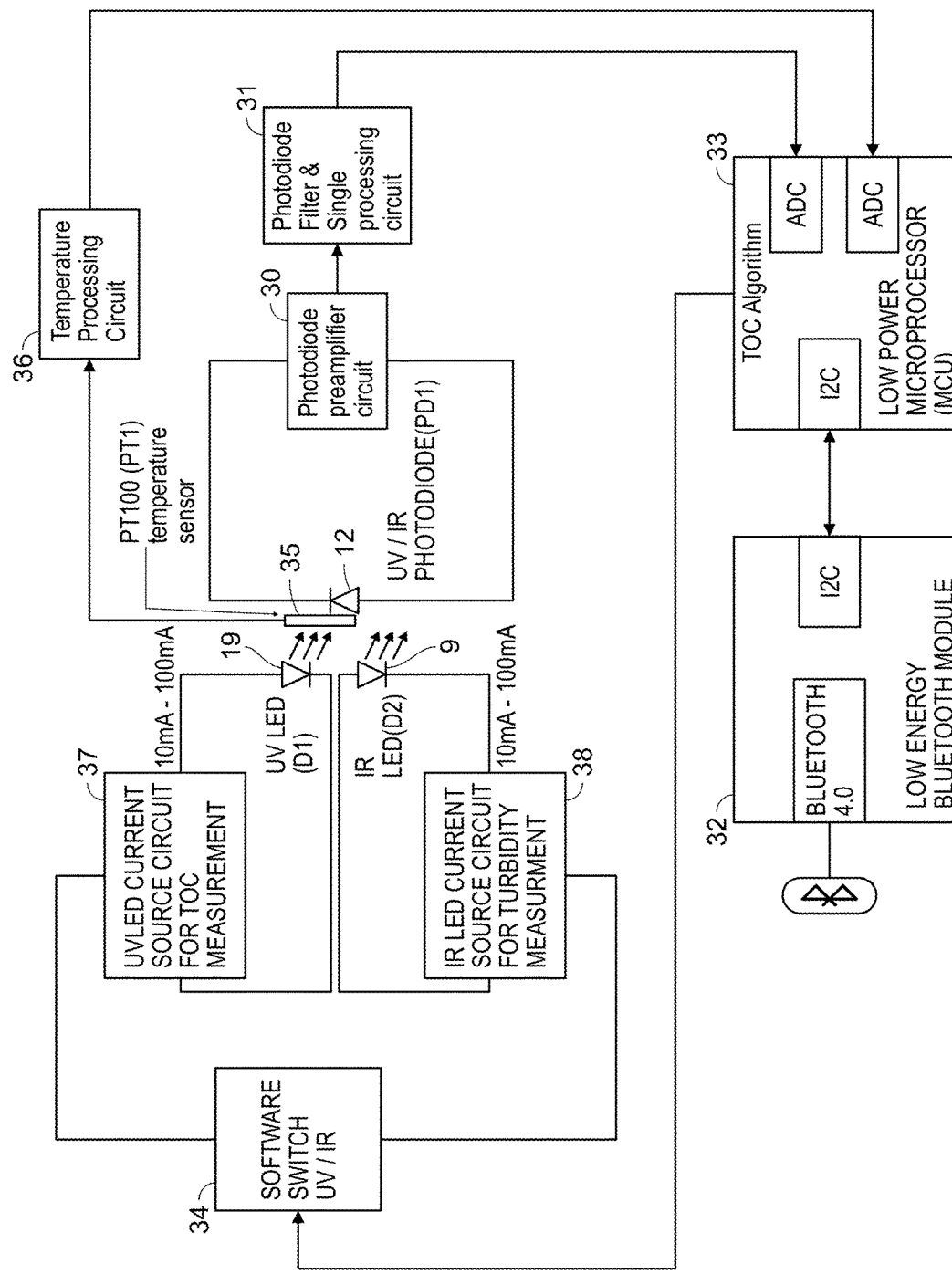
FIG. 6 is an exemplary measurement circuit for the device.

A sample schematic of a measurement circuit for the calculation of TOC is shown in FIG. 6. The circuits can be located on one or more PCBs, such as 8 and 9. Photodiode receiver 12 capable of receiving UV254 and/or IR transmits current proportional to light absorbed to preamplifier circuit 30. Filter & average and/or additional signal processing may be performed by circuit 31. Furthermore, temperature sensor 35 may transmit temperature near the photodiode to temperature processing circuit 36. UV, IR and temperature data is used to perform the TOC calculation by algorithm module 33.

Figure 5:
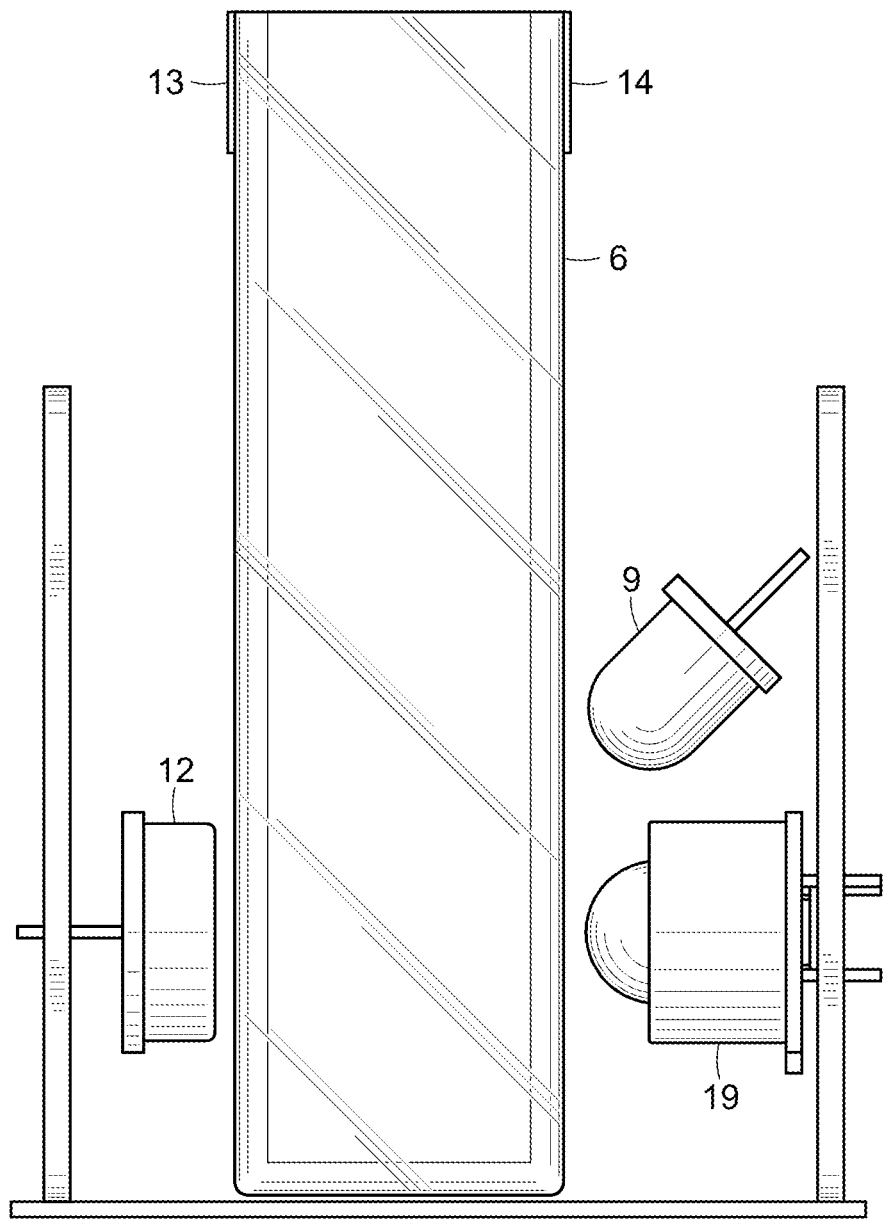
FIG. 5 is a side of an embodiment of the measurement chamber of the device.

In order to conserve power, the LEDs are activated only when the chamber 6 is substantially full. FIG. 5 demonstrates two different ways to implement this functionality. In a first example, conductive metal plates 13 and 14 are situated on each side of the top of chamber 6, such that together they form a capacitor. Fluid filling the chamber 6 causes voltage change, which causes the LED circuit to be activated. In a second example, by positioning an LED at an angle—such as the 45 degree angle of LED 9 depicted by example in FIG. 5—light from the LED is not received by a receiver until the water level in chamber 6 exceeds that of the light source 9, due to refraction. Thus, the detection of light from LED 9 may be used to activate the UV254 LED and/or measurement circuit.

As described here, the preferred embodiment requires a mere 500 μA of power consumption when the circuit is not activated. Upon activation of UV254 and the TOC measurement circuit, power consumption rises to around 15 mA, but only for the time needed to complete the calculation. Thus, the use of LEDs, automatic activation, high quantum efficiency photodiodes, and accurate signal processing each contribute to the low power consumption of the device.

Power may be delivered by any means, including by battery pack 20 as depicted, or any other means including, but not limited to, AC/DC, solar and hydroelectric power. The low power requirement of the device enables the use of low power sources such as solar. Solar panels may be located directly on the outer casing of the device. The battery pack may be removable, replaceable, and/or rechargeable by USB or a wall outlet connection.

Other embodiments may comprise any combination and types of receivers. The positioning of receivers depicted in the drawings is exemplary, and receivers may be located anywhere on, near or inside of the chamber. Receivers may be any type of receivers currently known in the art, including, but not limited to, photometric sensors for receiving light, temperature probes for determining temperature, and electrodes for measuring resistance. For instance, Total Dissolved Solids (TDS) correlate with conductivity and may be measured by determining the resistance between two electrodes within the sample chamber. TDS, or Total Dissolved Solids, is a measure of the combined inorganic and organic substances in the water, and as such is another useful measure of contamination. As another example, voltage between an electrode within water in the sample chamber, and another electrode within a fixed pH liquid, may be used to determine pH of the water.

Figure 7:
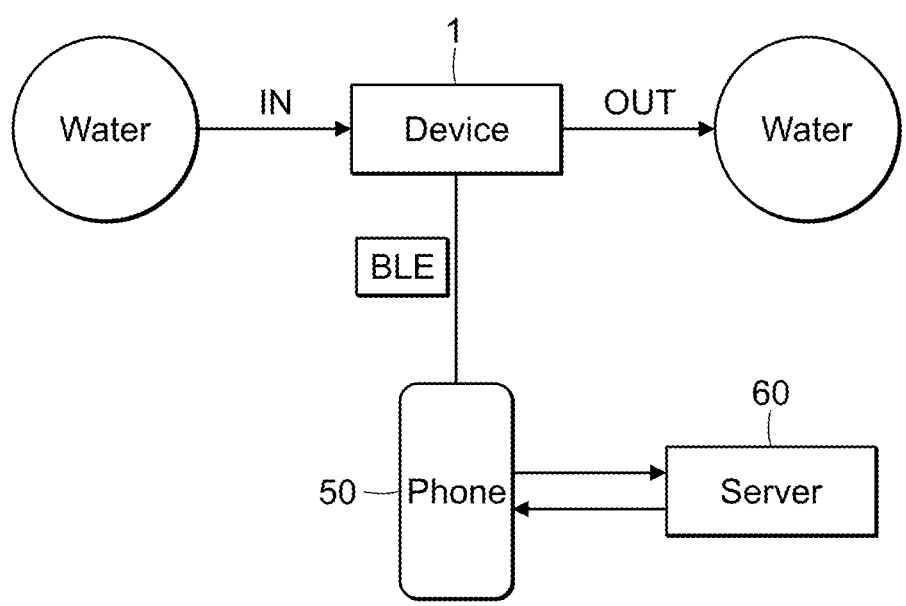
FIG. 7 is a system schematic of the device operable to send data to a remote apparatus such as a phone.

The device may comprise a low-power Bluetooth module 32 to transmit contamination information to a remote apparatus operable to receive data from the device. FIG. 7 is a schematic showing the device 1 in Bluetooth or other wireless connection to smartphone 50. Smartphone device 50 may also be capable of sending and receiving data to server 60 for the collection and management of user water contamination data. The display of contamination information need not be remote, however, indeed may be anywhere on the device itself, such as on its external casing. For instance, a screen or LED signal can be incorporated onto the outside of the device.

Figure 8:
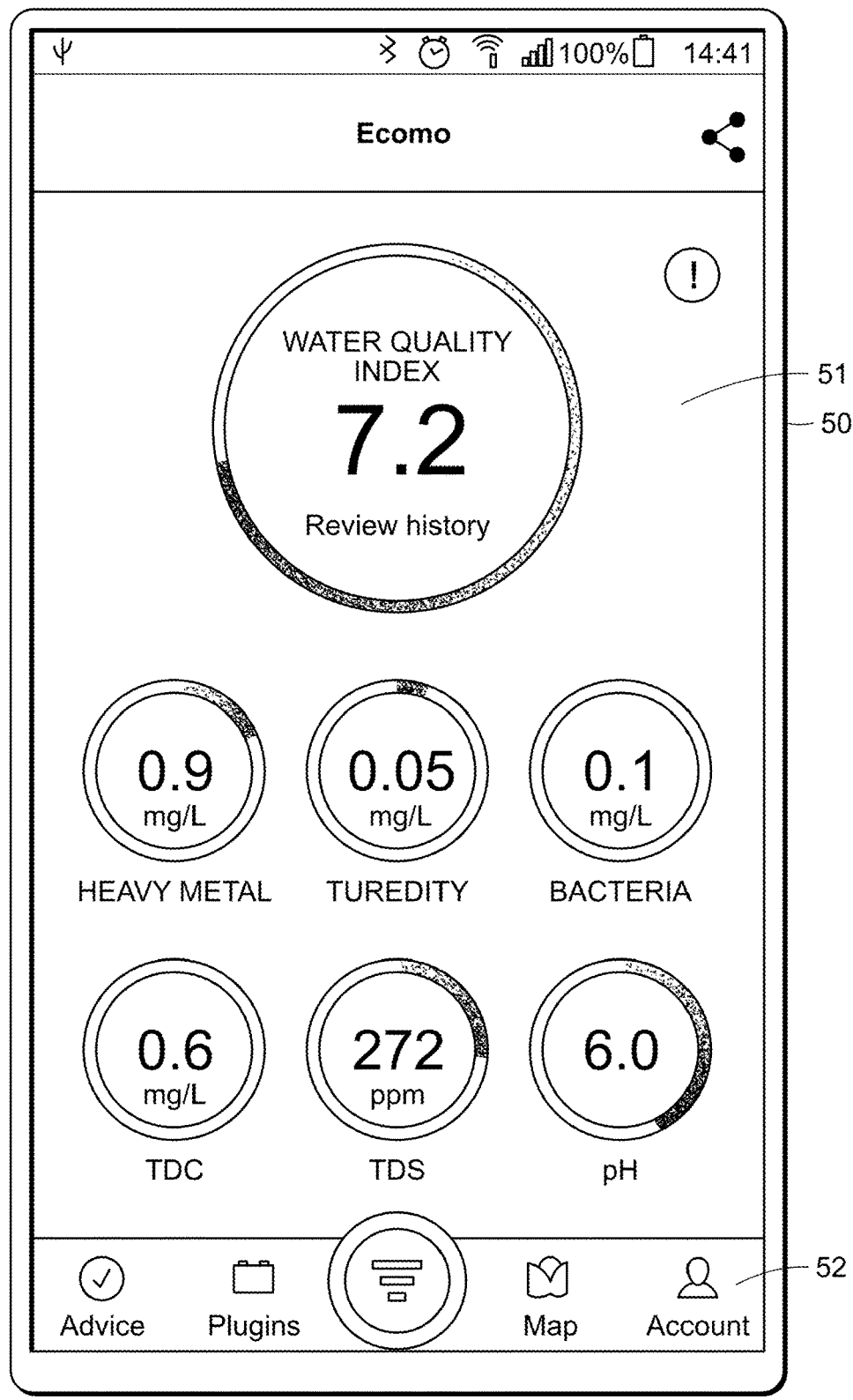
FIG. 8 is a sample remote apparatus displaying data received from the device.
Figure 9:
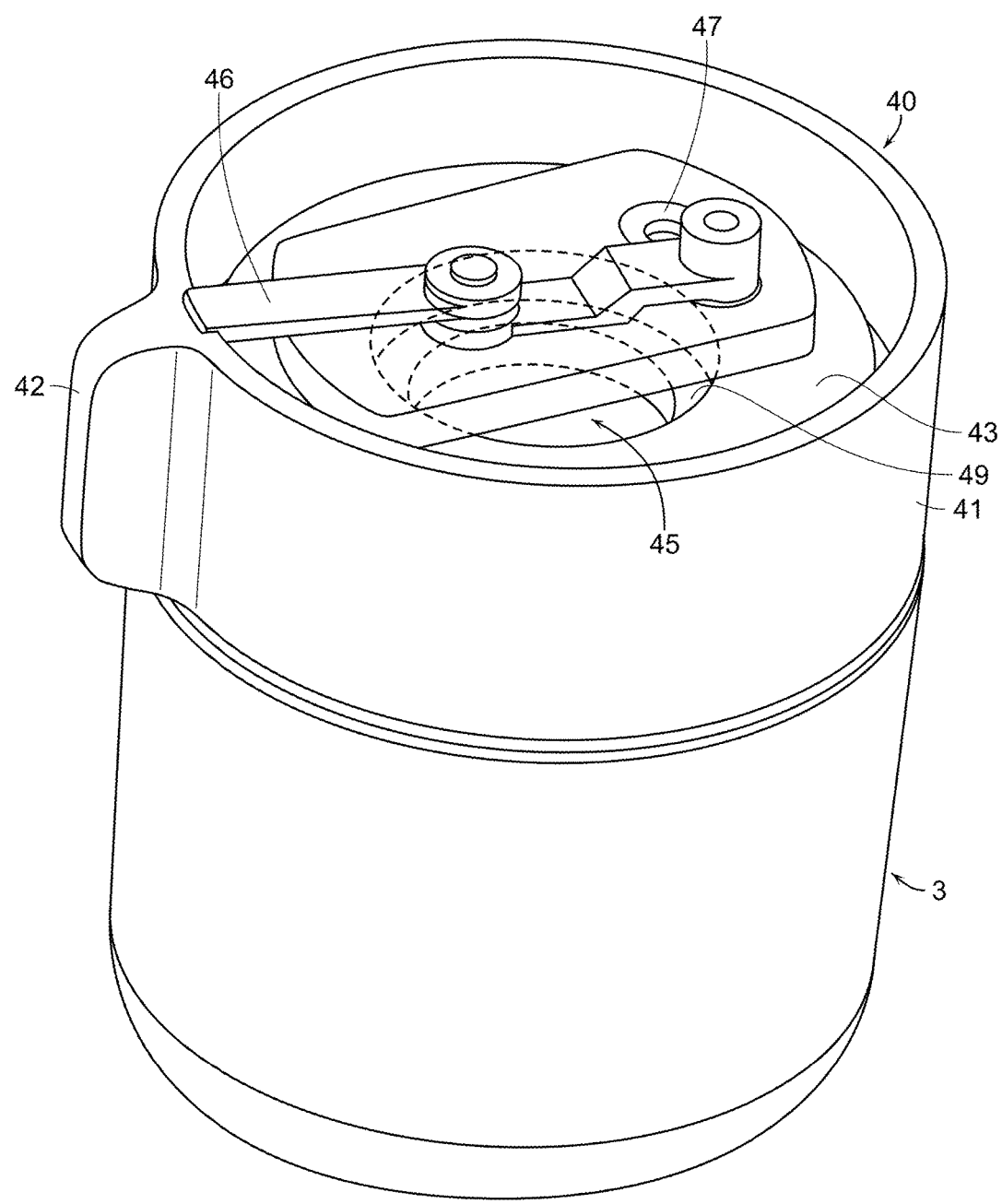
FIG. 9 is a side perspective view of the inside of an embodiment of the device.
Figure 10:
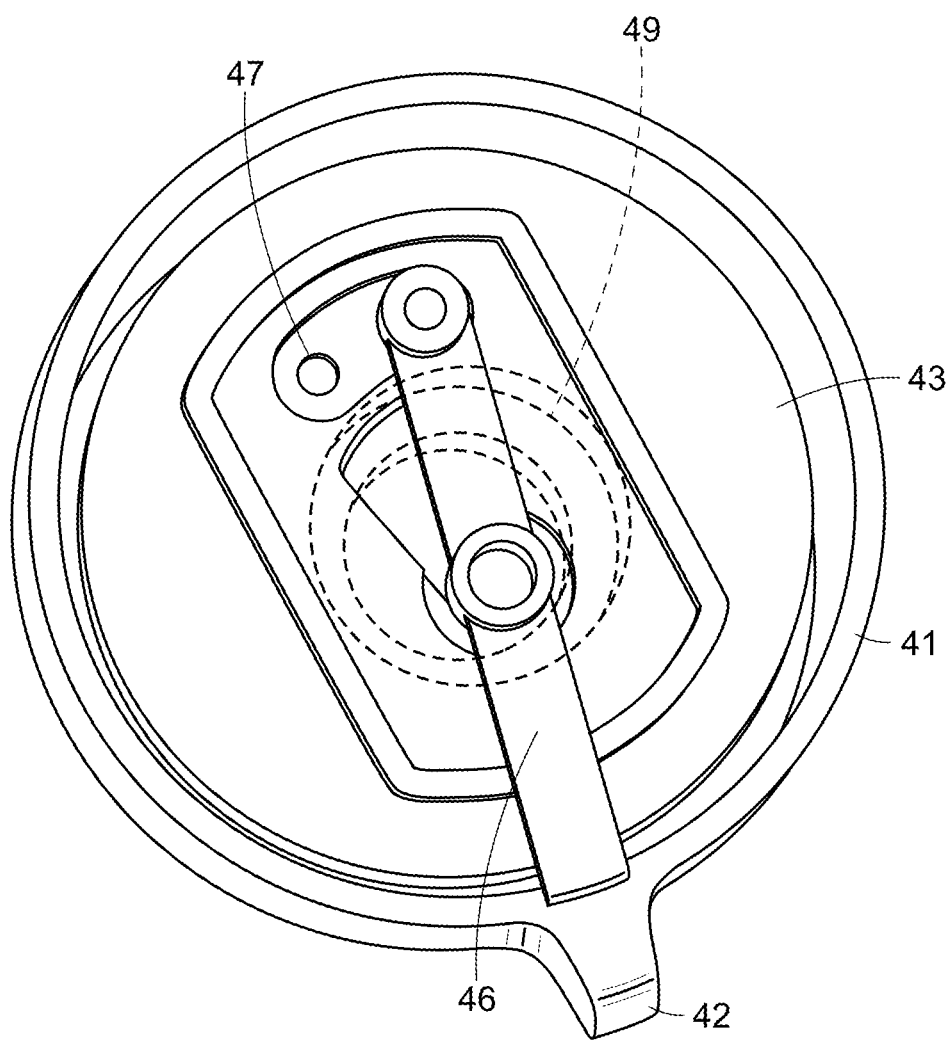
FIG. 10 is a top view, in partial perspective, of an embodiment of the device.

The remote apparatus 50 can receive and process contamination data according to methods already known in the art. The remote apparatus can be programmed to receive and display data as the programmer desires. For instance, FIG. 8 shows a display screen 51 on user device 50, the display screen showing current levels of heavy metals, turbidity, bacteria, TOC, TDS and PH that has been transmitted from device 3.

Filter Unit

The device can further comprise optional filter unit 40. The filter unit comprises a compartment 43 holding a replaceable filter 49. Filter functionality can be turned "on and off" such that the user can have filtered water only when needed, conserving the lifetime of the filter. The on/off functionality is incorporated into the design of the device, intuitively operated by rotating the filter unit around the axis of tap 2. When housing 41 is rotated, an internal switch 46 coupled to the filter unit housing 41 reveals an opening 47 leading to filter compartment 43. Filter compartment 43 holds a replaceable filter 49. The filter 49 can be a cylindrical carbon filter that fits into cylindrical filter core 43 or it may be any type of commercially available filter. Water flows through the filter and ultimately out of the filter unit through exit 45. When opening 47 is covered, water from the tap flows around the filter compartment 43 and out of exit 45 without filtering. Thus, water flowing into entrance 53 of the filter unit will either be diverted by switch 46 through the filter compartment 43 and filter 49 or it will flow around filter compartment 43 directly to the exit 45. Filter unit housing 41 preferably comprises an external switch 42 as a lever to facilitate rotation. In the embodiment of the device depicted, water leaving exit 45 ultimately flows into opening 4 of the measurement unit 3. However, the device can comprise either the measurement unit 3, the filter unit 40, or both. An adapter 54 can be provided to fit the device onto any consumer tap.

Optionally, an electronic detector can be incorporated into the device to signal when the filter has been activated. For instance, a small magnet coupled to the filter unit and a magnetic sensor coupled to the measurement unit can be used to activate a signal when the filter unit has been rotated into the "on" position. Using the water purity information supplied by the measurement unit, the user can determine when a new filter is needed. When water quality at a tap diminishes and its user is made aware by the device or remote display 51, the user may desire to install a new water filter.

The invention claimed is:

1. A device for installation onto a tap comprising:
    a filter unit operable to filter water when the tap is operated;
    a chamber located below the filter unit, wherein the chamber receives a flow of fluid from the tap when the tap is operated;
    an ultraviolet LED that when the chamber is substantially full at least one photometric receiver measures the amount of ultraviolet light absorbed by fluid within the chamber; and
    a circuit configured to convert ultraviolet light absorbance from the photometric receiver to generate a signal for transmitting contaminant data;
        wherein the filter unit comprises a housing that is rotatable around the axis of the tap;
        a compartment, situated in-line between the tap and the exit, enclosed by the housing, and containing a filter; and
        a switch rotatable around the axis to switch between covering and uncovering an opening located above and leading to the compartment, and coupled to the housing, wherein when the housing is rotated the switch is rotated, diverting water to the compartment, or to the chamber.

2. The device of claim 1 wherein the chamber receives flow from the bottom of the chamber to fill the chamber.

3. The device of claim 1 further comprising two metal conductors, situated on opposite sides of the top of the chamber, such that when the chamber is substantially full a capacitive charge between the two metal conductors activates the LED.

4. An apparatus operable to receive data from a device installed on a tap, the data relating to the tap water, wherein the device comprises:
    a filter unit operable to filter water when the tap is operated;
    a chamber located below the filter unit, wherein the chamber receives a flow of fluid from the tap when the tap is operated;

an ultraviolet LED that when the chamber is substantially full is activated to emit light to the chamber such that at least one photometric receiver measures the amount of ultraviolet light absorbed by fluid within the chamber; and a circuit configured to convert ultraviolet light absorbance from the photometric receiver to generate the data relating to the tap water;

wherein the filter unit comprises: a housing that is rotatable around the axis of the tap;

a compartment, situated in-line between the tap and the exit, enclosed by the housing, and containing a filter; and a switch rotatable around the axis to switch between covering and uncovering an opening located above and leading to the compartment, and coupled to the housing, wherein when the housing is rotated the switch is rotated, diverting water to the compartment, or to the chamber.

5. The device of claim 4 wherein the chamber receives flow from the bottom of the chamber to fill the chamber.

6. The device of claim 4 further comprising two metal conductors, situated on opposite sides of the top of the chamber, such that when the chamber is substantially full a capacitive charge between the two metal conductors activates the LED.

7. A device for installation onto a tap comprising:
a housing that is rotatable around the axis of the tap;
an exit for dispensing fluid, the exit of the device situated in-line with the tap;
a compartment, situated in-line between the tap and the exit, enclosed by the housing, and containing a filter; and
a switch rotatable around the axis to switch between covering and uncovering an opening located above and leading to the compartment, and coupled to the housing, such that when the housing is rotated the switch is rotated, diverting water to the compartment, or to the exit.

8. The device of claim 7, further comprising:
a chamber located between the compartment and the exit, wherein the chamber receives water diverted from the compartment;
an ultraviolet LED that, when the chamber is substantially full, is activated to emit light to the chamber such that at least one photometric receiver measures the amount of ultraviolet light absorbed by fluid within the chamber; and
a circuit configured to convert ultraviolet light absorbance from the photometric receiver and to generate a signal for transmitting contaminant data.

* * * * *